United States Patent [19]

Monte

[11] Patent Number: 5,380,752
[45] Date of Patent: Jan. 10, 1995

[54] METHOD FOR PREVENTING OXIDATION OF CRYSTALLINE STEROID ALCOHOLS IN CELLS, LIPOPROTEINS, AND CHYLOMICRONS

[76] Inventor: Woodrow C. Monte, 6411 S. River Dr., #65, Tempe, Ariz. 85283

[21] Appl. No.: 877,826

[22] Filed: May 1, 1992

[51] Int. Cl.⁶ ............................................. A61K 31/34
[52] U.S. Cl. .................................................. 514/474
[58] Field of Search ........................................ 514/474

[56] References Cited

U.S. PATENT DOCUMENTS 4,865,836  9/1989  Long, Jr. ............................ 424/5
4,954,521  9/1990  Sawyer et al. ..................... 514/474
4,959,362  9/1990  Terao et al. ....................... 514/231.5
5,114,716  5/1992  N'Guyen et al. ................... 424/401

*Primary Examiner*—Marianne M. Cintins
*Assistant Examiner*—Kimberly R. Jordan
*Attorney, Agent, or Firm*—Tod R. Nissle

[57] ABSTRACT

A method for preventing oxidation by the cells lining the blood vessels of the body of a crystalline steroid alcohol comprises incorporating in the bloodstream a composition comprising all ascorbyl monoester of a saturated aliphatic monocarboxylic acid containing from 12 to 18 carbon atoms per molecule.

6 Claims, No Drawings

METHOD FOR PREVENTING OXIDATION OF CRYSTALLINE STEROID ALCOHOLS IN CELLS, LIPOPROTEINS, AND CHYLOMICRONS

This invention relates to a method for preventing the oxidation of crystalline steroid alcohols in the body.

More particularly, the invention relates to a method for preventing the oxidation of cholesterol in the cells, lipoproteins, and chylomicrons of the body.

Cholesterol is a crystalline steroid alcohol $C_{27}H_{45}OH$ that is an essential constituent of animal cells and body fluids. Each cell in the human body includes membranes. Cholesterol is an important part of these membranes. The liver uses cholesterol to make bile acids. Bile acids are used by the body to aid in the digestion of food. Cholesterol is also important in the production of certain hormones and in other physiological processes. While all of the cells in the body can manufacture cholesterol, the liver produces the most cholesterol. Carrier molecules called lipoproteins transport cholesterol produced by the liver. Lipoproteins are produced by the liver. The lipoproteins are delivered by the bloodstream to cells throughout the body. There are three types of lipoproteins, high-density lipoproteins (HDL), low-density lipoproteins (LDL), and very low-density lipoproteins (VLDL). Cholesterol is also carried in chylomicrons which enter the bloodstream via the lymphatic system. Chylomicrons are produced by the small intestine.

High concentrations of LDL and VLDL's in the bloodstream have been implicated as a factor in certain diseases, particularly arteriosclerosis. Arteriosclerosis develops when plaque or deposits that contain cholesterol adhere to or form on the inner walls of the blood vessels. The plaque narrows the blood vessels and facilitate blockage of the blood vessels by blood clots. When a clot blocks an artery of the heart, a heart attack often results.

Before it is oxidized, cholesterol is, while being transported through the body in lipoproteins or chylomicrons, safe. Once, however, the cholesterol is oxidized, it takes on a form which promotes arteriosclerosis, possibly because macrophages absorb the oxidized cholesterol, die, and become the plaque which lines the arteries.

Arteries appear to be prime candidates for the formation of such plaque because they carry blood which is rich in oxygen. Since all cells in the body produce and may therefore oxidize cholesterol, the ready availability of oxygen in blood flowing through the arteries may, in theory, facilitate the oxidation of cholesterol in the cells lining the inner walls of the arteries and promote the formation on arterial walls of sites at which oxidized cholesterol more readily accumulates.

The oxidation of cholesterol and other crystalline steroid alcohols occurs in some individuals at greater rates than in other individuals, for reasons which are not fully understood. At any rate, the consensus is that reducing the amount of oxidized cholesterol produced by the body reduces the risk that arteriosclerosis will occurs and also, if arteriosclerosis does occur, reduces the rate at which plaque forms on the inner walls of blood vessels.

Accordingly, it would be highly desirable to provide a method for inhibiting, in whole or in part, the oxidation of a crystalline steroid alcohol by the body.

It would also be highly desirable to provide a method for inhibiting the oxidation of cholesterol and other crystalline steroid alcohols by the cells which comprise and line the inner walls of the blood vessels in the body.

These and other, further and more specific objects and advantages of the invention will be apparent to those skilled in the art from the following detailed description thereof.

Briefly, I have discovered a method of inhibiting the oxidation of crystalline steroid alcohols by cells lining the inner surfaces of veins and arteries. The method comprises incorporating in the bloodstream for absorption and dissolution in chylomicrons, high density lipoproteins, low density lipoproteins, and very low density lipoproteins a composition comprising an ascorbyl monoester of a saturated aliphatic monocarboxylic acid containing 12 to 18 atoms per molecule. The chylomicrons, high density lipoproteins, low density lipoproteins, and very low density lipoproteins are absorbed by the cells comprising the inner surfaces of the blood vessels to transport the ascorbyl monoester into the cells.

In another embodiment of my invention, I have discovered a method of inhibiting the oxidation of crystalline steroid alcohols carried in chylomicrons, high density lipoproteins, low density lipoproteins, and very low density lipoproteins in the blood stream of a patient. The method comprises incorporation in the bloodstream for absorption and dissolution in the chylomicrons, high density lipoproteins, low density lipoproteins, and very low density lipoproteins a composition comprising an ascorbyl monoester of a saturated aliphatic monocarboxylic acid containing 12 to 18 carbon atoms per molecule.

In still another embodiment of my invention, I have discovered a method of inhibiting the oxidation of crystalline steroid alcohols carried in chylomicrons, high density lipoproteins, low density lipoproteins and very low density lipoproteins in the bloodstream of a patient. The method comprises ingesting daily at least 0.05 grams of a composition comprising an ascorbyl monoester of a saturated aliphatic monocarboxylic acid containing 12 to 18 carbon atoms per molecule.

As used herein, the term "cholesterol" is defined as the crystalline steroid alcohol $C_{27}H_{45}OH$.

As used herein, the term "ascorbyl monoesters of fat acids" is defined as the monoesters of saturated aliphatic monocarboxylic acids containing from 12 to 18 carbon atoms per molecule with compounds of the ascorbic acid series having the general formula:

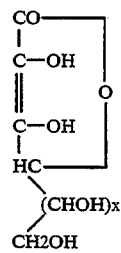

where x is 0 or a whole number not exceeding 3. Thus, the term "ascorbyl monoester of fat acids" is meant to include such compounds as myristyl, lauryl, palmityl, stearyl monoesters of d- and l-ascorbic acid, d- and l-isoascorbic acid, or of other compounds of the ascorbic acid series, used either singly or in combination.

The ascorbyl monoester is typically incorporated in the blood stream by ingestion and is preferably ingested on a daily basis. The amount of ascorbyl monoester ingested during a day is equal to or greater than about 0.075 gram, preferably a gram or more. Ingesting at any given time quantities of ascorbyl monoester less than about seventy-five milligrams is not preferred because such small quantities of ascorbyl monoester ordinarily are oxidized or destroyed in the intestinal tract, or are oxidized or destroyed before they enter the bloodstream of the patient. In particular, ingesting less than twenty milligrams of the ascorbyl monoester is not acceptable in the practice of the invention because such small quantities of the monoester do not survive transit through the intestine to the bloodstream. If desired, the ascorbyl monoester can be administered intravenously or by any other method which permits the monoester to reach the bloodstream of the patient before the monoester is oxidized or otherwise disabled or destroyed. When the ascorbyl monoester is ingested, it can be in pill form combined with vitamins, minerals, food products, fats, or any other desired composition safe for human consumption.

The ascorbyl monoesters used in the practice of the invention can be absorbed in and dissolved in the chylomicrons and lipoproteins carried in the bloodstream. The monoesters are believed to perform a sacrificial function. Oxygen which is in or enters the lipoproteins or chylomicrons is attracted first to the ascorbyl monoesters. The ascorbyl monoesters "consume" the oxygen and are sacrificially destroyed. If no ascorbyl monoesters are present, the oxygen turns its attention to oxidizing the cholesterol carried in the lipoproteins and chylomicrons.

The ascorbyl monoesters used in the invention function like a vaccine in that they are sacrificial, like the weakened antibodies of a vaccine; in that they help prevent or lessen the effects of a serious disease; in that they can be administered orally or intravenously like some vaccines; in that, like most vaccines, more than one administration of the monoester is preferred; and, in that, like vaccines, they provide ongoing continuous protection against a disease. These vaccine-like characteristics, along with the ready daily dietary administration of the ascorbyl monoesters, make the words "dietary vaccine" an apt description of the monoesters administered in the invention. Another dietary vaccine which is similar in ease of administration and in the low cost of producing the dietary vaccine is described in U.S. Pat. No. 4,931,432 for "DIETARY VACCINE FOR INHIBITING METABOLISM OF METHANOL".

The following examples depict the presently preferred embodiments of the invention for the purpose of illustrating the practice thereof and not by way of limitation of the scope of the invention. In the examples, all proportions are by weight, unless otherwise noted.

EXAMPLE 1 l-Ascorbyl Palmitate, the palmitic acid monoester of l-ascorbic acid, is prepared by dissolving 3.8 grams of l-ascorbic acid and 10.3 grams of palmitic acid in 100 cc of 95 percent sulfuric acid at essentially room temperature. The solution is allowed to stand for about 16 hours after which the reaction mixture is poured slowly and with vigorous stirring into about 500 grams of chopped ice. The stirring is continued until the oily phase of the mixture has solidified. The mixture is then extracted with ethyl ether and the ether extract is washed with water until the washings are substantially free of mineral acid. The ether extract is then dried and evaporated to dryness and the residue remaining is powdered and washed by decantation with 200 to 300 cc. of petroleum ether (boiling range 35 degrees to 60 degrees C.), thereby removing the unreacted palmitic acid from the reaction product. The white solid residue is insoluble in petroleum ether and consists essentially of ascorbyl monopalmitate. The yield is good. This procedure for the manufacture of ascorbyl monopalmitate is recited in U.S. Pat. No. 2,383,816 to Riemenschneider et al.

EXAMPLE 2

Two hundred milliliters of blood is removed from an adult Caucasian male who is thirty-four years of age, in good health, and weighs 160 pounds. One hundred milliliters of the blood is used to test the blood to confirm that the albumin, anticoagulant, coagulant, fibrin, gamma globulin, globulin, glucose, hemoglobin, iron, plasma, serum, red blood cells, white blood cells, and platelet in the blood all are within normal range and condition. Such testing of the blood confirms that the components of the blood and condition of the components are normal. The testing is also used to determine the quantity of cholesterol in the blood. The testing determines that cholesterol is present in a concentration of 200 milligrams per one deciliter of blood.

Fifty milliliters of the blood removed from the Caucasian male is immediately placed in a perfusion cell at room temperature and an anticoagulant is mixed in the blood to prevent clotting. The top of the cell is not covered. Oxygen is bubbled through the blood for a period of thirty minutes. The flow rate of oxygen through the blood and size of the bubbles of oxygen traveling through the blood are adjusted to approximate the rate at which blood traveling through the lungs is exposed to oxygen in the air inhaled into the lungs at sea level. At the end of the thirty minute period, the blood is tested to determine the quantity of oxidized cholesterol present in the blood. The test identifies four milligrams of oxidized cholesterol per one deciliter of blood.

The remaining fifty milliliters of the blood removed from the Caucasian male is immediately placed in a second perfusion cell at room temperature and an anticoagulant is mixed in the blood to prevent clotting. The top of the graduated cylinder is not covered. 0.5 milligrams of l-Ascorbyl palmitate are mixed with 9.5 milligrams of ethanol to form a palmitate-ethanol solution. The entire palmitate-ethanol solution is mixed in the blood. Oxygen is bubbled through the blood for a period of thirty minutes. At the end of the thirty minute period, the blood in the second perfusion cell is tested to determine the quantity of oxidized cholesterol present in the blood. The test does not detect any oxidized cholesterol in the blood. The flow rate of oxygen bubbled through the second perfusion cell and the size of the oxygen bubbles equals the flow rate and bubble size of the oxygen which was bubbled through the first perfusion cell during the thirty minute period noted in the paragraph immediately above.

EXAMPLE 3

Example 2 is repeated except that 5 milligrams of l-Ascorbyl palmitate is mixed into the second perfusion cell instead of the 0.5 milligrams of l-Ascorbyl palmitate. Similar results are obtained.

EXAMPLE 4

Example 2 is repeated except that 50 milligrams of 1-Ascorbyl palmitate is mixed into the second perfusion cell in place of the 0.5 milligrams of 1-Ascorbyl palmitate. Similar results are obtained.

EXAMPLE 5

Example 2 is repeated except that 0.5 milligrams of d-isoascorbyl palmitate is used in place of the 0.5 milligrams of 1-Ascorbyl palmitate. Similar results are obtained.

EXAMPLE 6

Example 2 is repeated except that 5 milligrams of d-isoascorbyl palmitate is used in place of the 0.5 milligrams of 1-Ascorbyl palmitate. Similar results are obtained.

EXAMPLE 7

Example 2 is repeated except that 50 milligrams of d-isoascorbyl palmitate is used in place of the 0.5 milligrams of 1-Ascorbyl palmitate. Similar results are obtained.

EXAMPLE 8

A one hundred milliliter aqueous solution containing 0.1 N solution of hydrochloric acid is prepared and placed in a graduated cylinder. The top of the cylinder is left open. Two grams of butter fat are mixed into the aqueous solution. One milligram of 1-Ascorbyl palmitate is mixed with nineteen milligrams of ethanol. The entire twenty milligrams ethanol-palmitate solution is added to the aqueous solution. The solution is stirred for three hours. At the end of the three hour period, the solution is tested for the presence of 1-Ascorbyl palmitate. The test does not detect any 1-Ascorbyl palmitate in the solution. When only small amounts of ascorbyl monoesters are ingested in the digestive tract of a human being, the monoesters are oxidized or destroyed in the digestive tract before they can be absorbed by the epithelial tissues which line the small intestine. Important in the practice of the invention is insuring that the quantity of ascorbyl monoesters ingested at any particular time is sufficient to insure that a significant quantity of the monoesters will reach the bloodstream either directly, by being absorbed and carried in host chylomicrons, or by being carried on or in some other host composition. Preferably, at least 75 milligrams of ascorbyl monoester is ingested at any one time, i.e., is ingested during a particular meal in the pill(s) or other carriers ingested at any given time.

EXAMPLE 9

Example 8 is repeated, except that two milligrams of 1-Ascorbyl palmitate are used in place of one milligram of 1-Ascorbyl palmitate. Similar results are obtained.

EXAMPLE 10

Example 8 is repeated, except that ten milligrams of 1-Ascorbyl palmitate are used in place of one milligram of 1-Ascorbyl palmitate. Similar results are obtained.

EXAMPLE 11

Example 8 is repeated, except that seventy-five milligrams of 1-Ascorbyl palmitate are used in place of one milligram of 1-Ascorbyl palmitate. The test conducted after the expiration of three hours detects ascorbyl palmitate present in the aqueous acidic solution.

EXAMPLE 12

A three gram sample of living cells is removed from the inner lining of the artery of a twenty year old male cadaver. The cells are of the same type and are in good health. A one gram portion of the cells is tested for the presence of cholesterol and oxidized cholesterol. Cholesterol is identified in the cells. Oxidized cholesterol is not detected in the cells. Another one gram portion of the sample is, to support the cells and prevent their death, immediately placed in a cell culture bottle using standard cell culture techniques. Five hundred milliliters of standard culture solution are in the dish and cover the cells. The solution includes serum, buffers, etc. and other necessary components in accordance with stand cell culture techniques. The solution is slowly circulated over the cells by a stirrer in the dish. Lipoproteins are mixed into the solution in a concentration similar to that found in blood. The alkalinity of the solution is comparable to the alkalinity of blood. The dish is not covered. The solution is maintained at a temperature of about 98.6 degrees Fahrenheit. Oxygen is bubbled through the cell culture solution. The oxygen is bubbled through the solution dish at a rate and using a bubble size(s) which simulates the exposure of the cells to oxygen in the patient's artery. After thirty minutes, the cells are tested for the presence of oxidized cholesterol. Oxidized cholesterol is detected.

The remaining one gram portion of the sample is also, to support the cells and prevent their death, immediately placed in cell culture bottle using standard cell culture techniques. Five hundred milliliters of standard cell culture solution is in the bottle and covers the cells. The solution includes serum, buffers, etc. and other components in accordance with standard cell culture techniques. The solution is slowly circulated over the cells by a stirrer in the dish. Lipoproteins are mixed into the solution in a concentration similar to that found in blood. The alkalinity of the solution is comparable to the alkalinity of blood. Five milligrams of 1-Ascorbyl palmitate is mixed with 95 milligram of ethanol. The entire ethanol-palmitate solution is mixed into the saline solution. The solution is maintained at a temperature of about 98.6 degrees Fahrenheit. Oxygen is bubbled through the solution. The oxygen is bubbled through the solution at a rate and using a bubble size(s) which simulates the exposure of the cells to oxygen in the patient's artery. After thirty minutes, the cells are tested for the presence of oxidized cholesterol. Oxidized cholesterol is not detected.

EXAMPLE 13

Example 12 is repeated, except fifty milligrams of 1-Ascorbyl palmitate is mixed into the cell culture solution instead of five milligrams of the 1-Ascorbyl palmitate. Similar results are obtained.

EXAMPLE 14

Example 12 is repeated, except five hundred milligrams of 1-Ascorbyl palmitate is mixed into the cell culture solution instead of five milligrams. Similar results are obtained.

EXAMPLE 15

Example 12 is repeated, except five milligrams of d-isoascorbyl palmitate is mixed into the cell culture solution instead of the five milligrams of l-Ascorbyl palmitate. Similar results are obtained.

EXAMPLE 16

Example 2 is repeated for each individual in a test group. Each member of the test group is in good health. The test group includes the twenty-five individuals listed in TABLE I. The results for each member of the test group are similar to the results obtained in Example 2.

TABLE I

Profile Data for Members of Test Group

| Member | Sex | Weight (Pounds) | Age (Yrs) | Race | Cholesterol Level (milligrains per 1 deciliter) |
|---|---|---|---|---|---|
| 1 | F | 96 | 16 | Caucasian | 192 |
| 2 | F | 102 | 20 | Caucasian | 202 |
| 3 | F | 120 | 23 | Caucasian | 230 |
| 4 | F | 134 | 38 | Caucasian | 242 |
| 5 | F | 182 | 34 | Caucasian | 261 |
| 6 | F | 98 | 21 | Black | 190 |
| 7 | F | 109 | 28 | Black | 200 |
| 8 | F | 110 | 24 | Black | 204 |
| 9 | F | 135 | 20 | Black | 218 |
| 10 | F | 167 | 28 | Black | 240 |
| 11 | M | 141 | 14 | Caucasian | 194 |
| 12 | M | 158 | 18 | Caucasian | 201 |
| 13 | M | 170 | 32 | Caucasian | 204 |
| 14 | M | 197 | 48 | Caucasian | 220 |
| 15 | M | 240 | 44 | Caucasian | 267 |
| 16 | M | 138 | 10 | Black | 192 |
| 17 | M | 169 | 25 | Black | 207 |
| 18 | M | 180 | 33 | Black | 222 |
| 19 | M | 180 | 50 | Black | 238 |
| 20 | M | 264 | 43 | Black | 272 |
| 21 | F | 94 | 21 | Asian | 188 |
| 22 | F | 96 | 24 | Asian | 194 |
| 23 | M | 144 | 30 | Asian | 214 |
| 24 | M | 153 | 26 | Asian | 218 |
| 25 | M | 166 | 47 | Indian | 251 |

EXAMPLE 17

Examples 3 to 7 are repeated for each member of the test group of Example 16. The results for each member of the test group are similar to the results obtained in Examples 3 to 7.

Having described the invention in such terms as to enable those skilled in the art to understand and practice it, and having identified the presently preferred embodiments thereof, I claim:

1. The method of inhibiting the oxidation of the crystalline steroid alcohol cholesterol in cells lining the inner surfaces of veins and arteries, comprising the incorporating of a composition into the bloodstream for absorption and dissolution in chylomicrons, high density lipoproteins, low density lipoproteins, and very low density lipoproteins, said composition comprising an ascorbyl monoester of a saturated aliphatic monocarboxylic acid containing 12 to 18 atoms per molecule; wherein the chylomicrons, high density lipoproteins, low density lipoproteins, and very low density lipoproteins are absorbed by said cells to transport said ascorbyl monoester into said cells.

2. The method of inhibiting the oxidation of the crystalline steroid alcohol cholesterol carried in chylomicrons, high density lipoproteins, low density lipoproteins, and very low density lipoproteins in the blood stream of a patient, comprising incorporating a composition into the bloodstream for absorption and dissolution in the chylomicrons, high density lipoproteins, low density lipoproteins, and very low density lipoproteins, said composition comprising an ascorbyl monoester of a saturate aliphatic monocarboxylic acid containing 12 to 18 carbon atoms per molecule.

3. The method of inhibiting the oxidation of the crystalline steroid alcohol cholesterol carried in chylomicrons, high density lipoproteins, low density lipoproteins, and very low density lipoproteins in the blood stream of a patient, comprising ingesting daily at least 75 milligrams of a composition comprising an ascorbyl monoester of a saturated aliphatic monocarboxylic acid containing 12 to 18 carbon atoms per molecule.

4. The method of claim 1 wherein the step of incorporating a composition into the bloodstream for absorption and dissolution in chylomicrons, high density lipoproteins, low density lipoproteins, and very low density lipoproteins, said composition comprising an ascorbyl monoester of a saturated aliphatic monocarboxylic acid containing 12 to 18 atoms per molecule, is replaced by the step of incorporating a composition into the bloodstream for absorption and dissolution in chylomicrons, high density lipoproteins, low density lipoproteins, and very low density lipoproteins, said composition comprising ascorbyl palmitate.

5. The method of claim 2 wherein the step of incorporating a composition into the bloodstream for absorption and dissolution in chylomicrons, high density lipoproteins, low density lipoproteins, and very low density lipoproteins, said composition comprising an ascorbyl monoester of a saturated aliphatic monocarboxylic acid containing 12 to 18 atoms per molecule, is replaced by the step of incorporating a composition into the bloodstream for absorption and dissolution in chylomicrons, high density lipoproteins, low density lipoproteins, and very low density lipoproteins, said composition comprising ascorbyl palmitate.

6. The method of claim 3 wherein the step of ingesting daily at least 75 mg of a saturated aliphatic monocarboxylic acid containing 12 to 18 atoms per molecule, is replaced by the step of ingesting daily at least 75 mg of ascorbyl palmitate.

* * * * *